US011087876B2

(12) United States Patent
Dejima

(10) Patent No.: US 11,087,876 B2
(45) Date of Patent: Aug. 10, 2021

(54) SPECIMEN ANALYSIS APPARATUS

(71) Applicant: HORIBA, Ltd., Kyoto (JP)

(72) Inventor: Yutaka Dejima, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 230 days.

(21) Appl. No.: 16/034,715

(22) Filed: Jul. 13, 2018

(65) Prior Publication Data

US 2019/0019580 A1 Jan. 17, 2019

(30) Foreign Application Priority Data

Jul. 14, 2017 (JP) .............................. JP2017-138411

(51) Int. Cl.
*G16H 40/63* (2018.01)
*G01N 35/00* (2006.01)

(52) U.S. Cl.
CPC ....... *G16H 40/63* (2018.01); *G01N 35/00623* (2013.01); *G01N 35/00663* (2013.01); *G01N 35/00722* (2013.01); *G01N 2035/009* (2013.01); *G01N 2035/0091* (2013.01); *G01N 2035/00673* (2013.01)

(58) Field of Classification Search
CPC ........ G16H 30/20; G16H 50/30; G16H 50/20; G16H 30/40; G16H 15/00; G16H 20/10; G16H 40/63; G01N 2035/0091; G01N 2035/009; G01N 1/00; G01N 35/00; G01N 2035/00178; G01N 35/00623; G01N 35/0063; G01N 35/00722; G01N 2035/00673; G06Q 50/22–24
See application file for complete search history.

(56) References Cited

U.S. PATENT DOCUMENTS

| 8,335,662 B2 * | 12/2012 | Wakamiya | ............... G06F 17/40 |
| 9,157,924 B2 * | 10/2015 | Yamato | ............... G01N 35/1004 |
| 2006/0190195 A1 * | 8/2006 | Watanabe | ............... G16H 10/40 |
| | | | 702/32 |
| 2008/0012892 A1 | 1/2008 | Imoto | |
| 2009/0215183 A1 * | 8/2009 | Takehara | ............... G01N 35/02 |

(Continued)

FOREIGN PATENT DOCUMENTS

| EP | 2309277 | * | 4/2001 | ............. G01N 35/00 |
| EP | 2040081 | * | 3/2009 | ............. G01N 35/00 |

(Continued)

OTHER PUBLICATIONS

European Patent Office, Extended European Search Report Issued in Application No. 18183429.2, dated Dec. 20, 2018, Germany, 7 pages.

(Continued)

*Primary Examiner* — Robert A Sorey
(74) *Attorney, Agent, or Firm* — Alleman Hall Creasman & Tuttle LLP

(57) ABSTRACT

The specimen analysis apparatus of the present invention comprises a measuring part; a display part; and a control part. The control part controls the measuring parts, displays on the display part an alarm display region displaying an alarm of a failure occurred in the measuring part, and a recovery operation display region displaying a recovery operation to cancel the alarm displayed in the alarm display region, and, when multiple alarms have occurred, displays multiple recovery operations to cancel them in the order of from higher priority to lower priority.

3 Claims, 4 Drawing Sheets

(56) References Cited

U.S. PATENT DOCUMENTS

| | | | |
|---|---|---|---|
| 2009/0292492 A1* | 11/2009 | Nishida | G01D 18/00 |
| 2011/0316713 A1* | 12/2011 | Okubo | G01N 35/026 |
| | | | 340/673 |
| 2012/0036944 A1* | 2/2012 | Chida | G01N 35/00613 |
| | | | 73/863.01 |
| 2012/0237400 A1* | 9/2012 | Ikeda | G01N 35/00712 |
| | | | 422/82.02 |
| 2012/0282155 A1 | 11/2012 | Kuwano et al. | |
| 2014/0341780 A1 | 11/2014 | Ishii | |
| 2015/0357824 A1* | 12/2015 | Hasegawa | H02J 4/00 |
| | | | 307/38 |
| 2016/0109473 A1 | 4/2016 | DeMarco | |

FOREIGN PATENT DOCUMENTS

| | | | |
|---|---|---|---|
| EP | 2040081 A2 | 3/2009 | |
| EP | 2309277 A1 | 4/2011 | |
| JP | 2008051532 * | 8/2006 | G01N 35/00 |
| JP | 2007140918 A | 6/2007 | |
| JP | 2008012868 A | 1/2008 | |
| JP | 2009074887 A | 4/2009 | |
| JP | 2009281847 A | 12/2009 | |
| JP | 2011075378 A | 4/2011 | |
| JP | 2012145997 A | 8/2012 | |
| JP | 2012163567 A | 8/2012 | |
| JP | 2012233807 A | 11/2012 | |
| JP | 2014035762 A | 2/2014 | |
| JP | 2014228285 A | 12/2014 | |

OTHER PUBLICATIONS

Japan Patent Office, Office Action Issued in Application No. 2017138411, dated Apr. 6, 2021, 3 pages.

\* cited by examiner

SPECIMEN ANALYSIS APPARATUS

FIELD OF THE INVENTION

The present invention relates to a specimen analysis apparatus for analyzing specimens such as blood, urine and the like.

BACKGROUND OF THE INVENTION

Conventionally, automatic analyzers that perform analysis (including particle counting) of specimens such as blood, urine and the like are used in various medical institutions and the like. This type of automatic analysis apparatus is generally constituted of a measuring part for performing specimen measurements and a control part for controlling the action of the measuring part. The measuring part includes devices relating to the measurement such as a driving part having a piping system containing a sampling nozzle and a driving unit for driving the system, a reagent-containing part, a measuring chamber, various pumps and the like. For example, in hematological analysis (including blood cell counting), a sampling nozzle sucks a given amount of blood contained in a specimen container, dispenses same to one or more measuring chambers, and also injects reagents etc., and the measurement is performed in the measuring chamber. In the measurement, in addition to control of the action of the measuring part, the control unit also analyzes the measurement data obtained from the measuring part (e.g., patent document 1 and the like).

In recent years, attempts have been made to improve the operability of this type of analysis apparatus besides improving the measurement accuracy of the apparatus and improving the measurement function. For example, an apparatus provided with a display part for displaying an alarm indicating the problem and a restoring operation for canceling the alarm when some failure occurs in the measuring part of the apparatus is known (e.g., patent document 2). That is, in this apparatus, when a failure occurs in the measuring part, the user looks at the display part and can recognize the alarm and the recovery operation for canceling the alarm, and perform the recovery operation.

PATENT DOCUMENT 1 JP-A-2014-228285
PATENT DOCUMENT 2 JP-A-2012-163567

However, when multiple failures occur in the measuring part and multiple alarms are displayed on the display part of the above-mentioned conventional apparatus, the recovery operation of each alarm in the plurality of alarms (i.e., respective recovery operations to solve the individual problems) are all displayed on the display part and the user does not know in what order the plurality of recovery operations should be performed. For example, when failures of alarm 1 "reagent shortage", and alarm 2 "door of the apparatus is open" have occurred, recovery operation 1 to cancel alarm 1 ("replace reagent and perform blank measurement") and recovery operation 2 to cancel alarm 2 ("close door of apparatus") are displayed on the display part. If recovery operation 1 is performed first, the driving part operates with the door of the apparatus open and it is dangerous (actually, interlock is applied on software and operation cannot be executed). That is, the order of execution priority of the plurality of recovery operations displayed on the display part is naturally determined in terms of the operational safety of the analysis apparatus; however, the users who do not know the details of the inner structure and operation mode of the apparatus cannot know this priority order.

The present invention has been made in view of such situation and an object thereof is to provide an analysis apparatus enabling the user to easily recognize, when multiple alarms have occurred and multiple recovery operations should be performed, the priority order of multiple recovery operations and rapidly execute the recovery operations in that priority order.

SUMMARY OF THE INVENTION

The major constitution of the present invention to achieve the above-mentioned object is as follows.
[1] A specimen analysis apparatus, comprising a measuring part for performing measurement for specimen analysis; a display part; and a control part, wherein
the control part controls the measuring part and analyzes measurement data from the measuring part,
displays on the display part an alarm display region displaying an alarm of a failure occurred in the measuring part, and a recovery operation display region displaying a recovery operation to cancel the alarm displayed on the alarm display region, and,
when multiple alarms have occurred, displays multiple recovery operations to cancel them in the order of from higher priority to lower priority.
[2] The specimen analysis apparatus according to [1], wherein the control part displays multiple recovery operations after revision to subtract the same operation from at least one recovery operation in the recovery operations having the same operation.
[3] The specimen analysis apparatus according to [1], wherein the control part displays, together with the multiple recovery operations, a command button for every recovery operation of the multiple recovery operations at a position adjacent to the display of each recovery operation.
[4] The specimen analysis apparatus according to any one of [1] to [3], wherein the command buttons for the multiple recovery operations turn inactive except a command button pressed for a recovery operation under execution.
[5] The specimen analysis apparatus according to any one of [1] to [4], wherein the control part displays a marker indicating whether or not the measuring part is capable of measurement while the alarm is displayed in the alarm display region.

In the specimen analysis apparatus according to the present invention, multiple alarms are displayed and multiple recovery operations are displayed in the order of high priority to low priority when multiple recovery operations should be performed. Therefore, the user who looks at the display part can recognize the priority order of multiple recovery operations, and can rapidly execute recovery operations in the order of priority.

In the specimen analysis apparatus according to the present invention, In addition, when multiple alarms are displayed requiring multiple recovery operations to be performed and multiple recovery operations include a recovery operation having the same operation, the multiple recovery operations are not only displayed in the order of high priority to low priority but displayed after revision to subtract the same operation from at least one recovery operation in the recovery operations having the same operation. Consequently, overlapping execution of the same operation can be reduced or avoided and the execution time of the recovery operation can be shortened.

In a preferable embodiment, the specimen analysis apparatus according to the present invention has a constitution in which the control part displays a marker indicating whether or not the measuring part is capable of measurement while the alarm is displayed in the alarm display region. When, for example, an alarm has occurred but there is a request to collect specimen measurement data without giving much weight to the importance of data reliability, the user looking at the display part can know whether the specimen can be measured without executing a recovery operation of the alarm. This enables flexible response meeting the situation.

Figure 1:
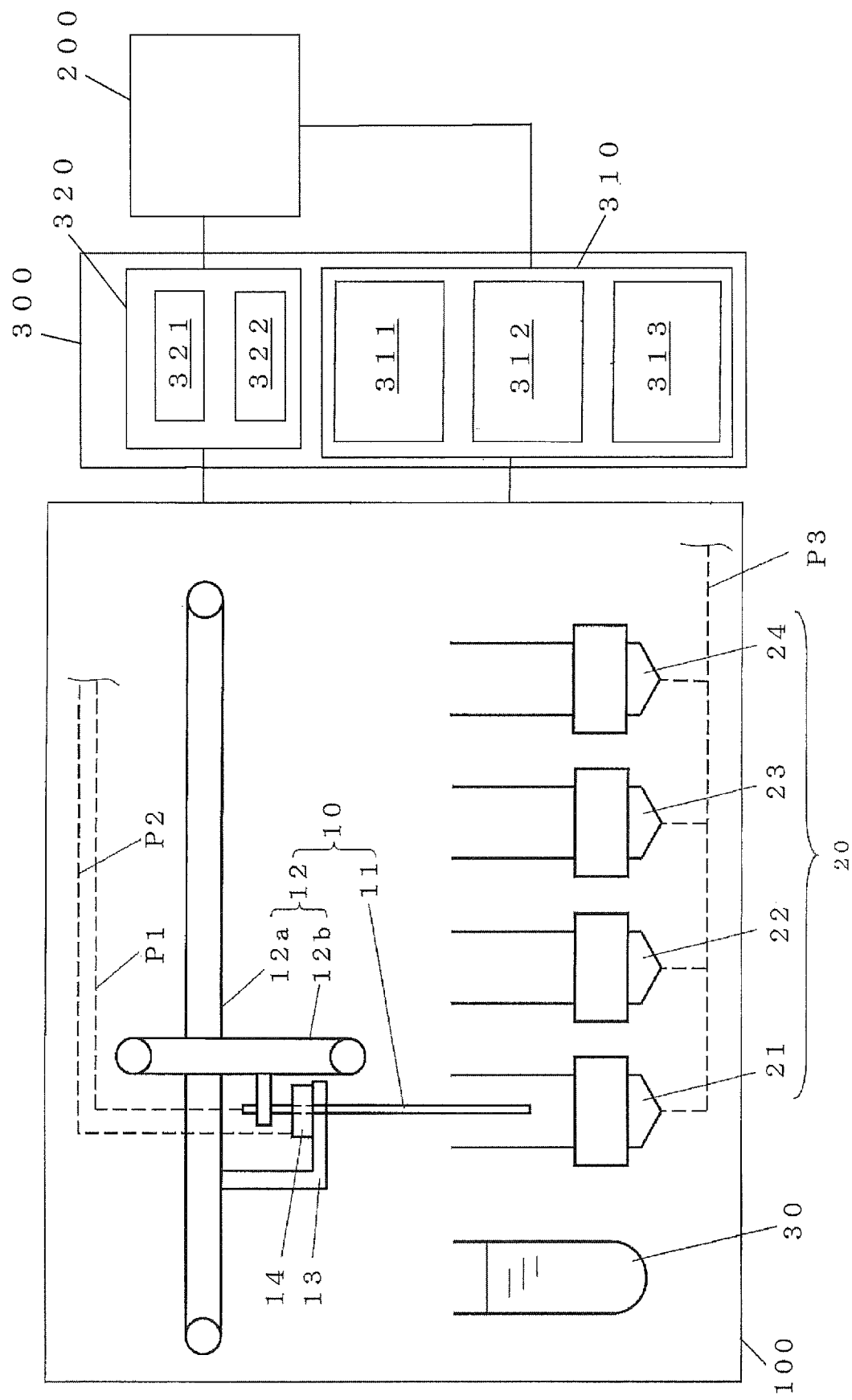
FIG. 1 is a block diagram showing one embodiment of the constitution of the specimen analysis apparatus according to the present invention. In this Figure, the relationship between the structural parts such as device, mechanism, piping and the like involved in the measurement and the control part is indicated using blocks, and the electric wiring is not shown.

In the Figures, the reference characters show the followings. 10; sampling nozzle driving part, 11; sampling nozzle, 12; driving unit, 20; measuring chamber, 30; specimen container, 100; measuring part, 200; display part, 300; control part, 50; guidance window, 51; alarm display region, 52; recovery operation display region.

DETAILED DESCRIPTION OF THE INVENTION

The embodiments of the specimen analysis apparatus according to the present invention (sometimes called the apparatus) are explained in detail below.

FIG. 1 shows one embodiment of the constitution of the main part of the specimen analysis apparatus according to the present invention. As illustrated in FIG. 1, the apparatus has at least a measuring part 100, a display part 200 and a control part 300. FIG. 1 is a block diagram showing the relationship among the measuring part 100 and the display part 200 and the control part 300, and the specific wiring is not shown.

The embodiments of FIG. 1 is an automatic blood analysis apparatus that performs counting and classification of blood cells and white blood cells, and the measuring part 100 contains a sampling nozzle driving part 10, a measuring chamber 20, pipings P1, P2, P3 and the like. The piping also contains various pumps, electromagnetic valve device, liquid cleansing agent tank, dilution liquid tank and reagent tank (these are not shown). The measuring chamber 20 is provided with a measuring chamber (BASO chamber) 21 for counting basophils, a measuring chamber (from the acronym for Lymphocyte, Monocyte, Neutrophil, Eosinophil, it is called LMNE chamber) 22 for classifying and counting lymphocytes, monocytes, neutrophils and eosinophils, a measuring chamber (RBC chamber) 23 for counting red blood cells, and a measuring chamber (WBC chamber) 24 for counting white blood cells and analyzing HGB (hemoglobin concentration). In the Figure, the symbol 30 is a specimen container, showing the specimen container 30 set in the apparatus.

As the display part 200, a flat panel display device such as a liquid crystal display device and the like (e.g., "touch panel" and the like), which is equipped with the function of an input device, is preferable. Such display and input device may be made to permit input on the CRT screen. A display and input device with a display screen functioning as an input part can be used without limitation. Analysis results obtained in the measuring part 100, alarm of failure occurring in the measuring part, recovery operation canceling the alarm, command button for commanding execution of a recovery operation and the like are displayed on the display screen of the display part 200.

Control Part

The control part 300 controls the measuring part 100 and the display part 200. The control part 300 may be constructed by a logic circuit and the like; however, a computer is appropriate, and may contain an input part (input means) such as keyboard, mouse and the like, external computing device, various driving devices (sensor, driver for motor and the like), external storage device and various interfaces.

The control part 300 has a measurement control part 310 and an action state management part 320. The measurement control part 310 is constituted to control motion of each part of the measuring part 100 (action of each part of sampling nozzle driving part, measurement action in each measuring chamber and the like), process for analyzing the measurement data sent from the measuring part (calculates), and output analysis results. In the embodiment of FIG. 1, a measurement control part 310 has an action control part 311 for controlling the action of each part of the measuring part 100, a data processing part 312 for processing the measurement data and outputting the analysis results, and a storage part 313 for storing the data processing results and the like. The action control part 311 receives a command signal input in the display part 200 for executing a recovery operation to cancel the alarm, and controls the action of the recovery operation in the measuring part 100.

The action state management part 320 monitors a signal sent when a failure is detected in the action of each part and constituent elements (drive system, parts, reagent etc.) of the measuring part 100, and performs a process for displaying an alarm of the failure and a recovery operation for cancelling the alarm on the display part 200. The action state management part 320 has a storage part 321 for previously storing data (alarm data) for displaying various failures occurring in the measuring part 100 as alarms including failure names, data (recovery operation data) for displaying sentences showing the contents of a recovery operation for cancelling the alarm, data (command button display data) for displaying a command button for executing the recovery operation and the like, and a data processing part 322 for processing (computing) to determine the details of the recovery operation and the order of priority of execution, which are to be displayed on the display part 200 according to the occurrence of a failure (occurrence of alarm).

As mentioned above, a recovery operation for cancelling a failure (alarm) may be constituted of a single operation or multiple operations depending on the content of the failure. A unit operation constituting these recovery operations forms a hierarchy from the action of the measuring part and the relation with the constituent element. The hierarchy data is also stored in advance in the storage part 321. To perform a certain recovery operation, other recovery operation may need to be performed, and the order of recovery operations is stored as hierarchical data. In the Examples, a nonoverlapping number indicating the order is stored for each recovery operation, and the recovery operation and the order are associated.

Assuming that the control part is constituted mainly of a computer, the content of the control is explained.

The control performed by the measurement control part 310 includes control of the action of each part of the measuring part 100 (action of each part of sampling nozzle driving part, measurement action in each measuring chamber and the like), and calculation processing for the analysis of measurement data sent from the measuring part 100, output, storage and the like of the analysis results, and the like. These controls are the same as general control of a conventionally-known analysis apparatus (patent document 1 etc.) and a detailed explanation is omitted.

The operation state management part 320 monitors the action of each part of the measuring part 100 and the state of the elements (parts, reagent etc.) constituting each part and, when a failure occurs in the measuring part 100, displays a failure alarm, a recovery operation to cancel the alarm and a command button for commanding execution of the recovery operation on the display part 200.

Figure 2:
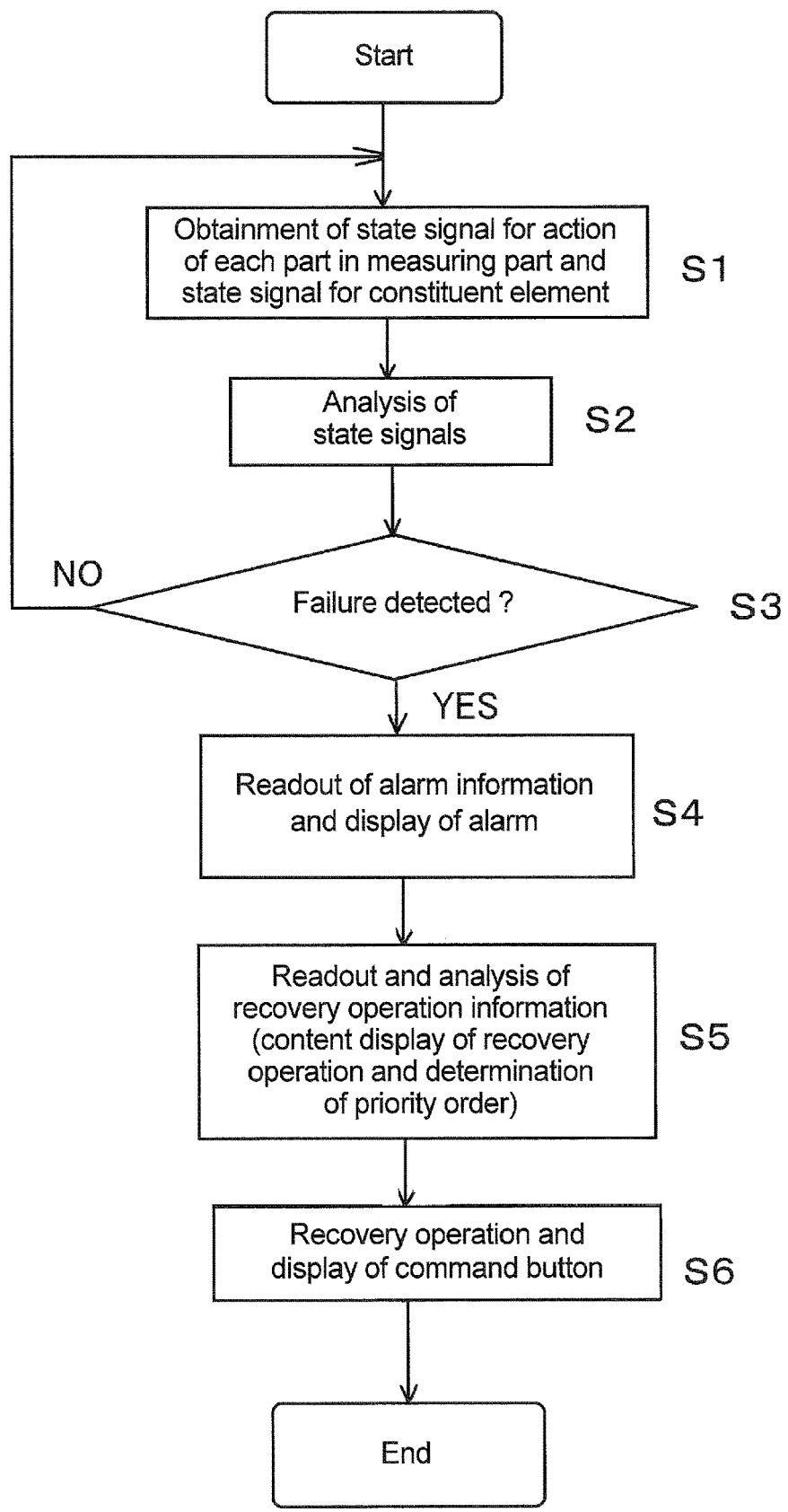
FIG. 2 is a flowchart showing one embodiment of the action of the specimen analysis apparatus according to the present invention.

FIG. 2 is a flowchart of processing procedures.

In step S1, signals are received. The signals are sent from the sensors provided on the constituent elements of sampling nozzle driving part 10, measuring chamber 20, pipings P1, P2, P3 etc. of the measuring part, and pump, electromagnetic valve device, liquid cleansing agent tank, dilution liquid tank, reagent tank and the like contained in the pipings P1, P2, P3.

In step S2, signals are analyzed, failure is detected and, when failure is absent in step S3, processing returns to step S1. On the other hand, when failure is detected in step S3, and an alarm of the failure detected in step S4 is displayed on the display part 200.

Figure 3:
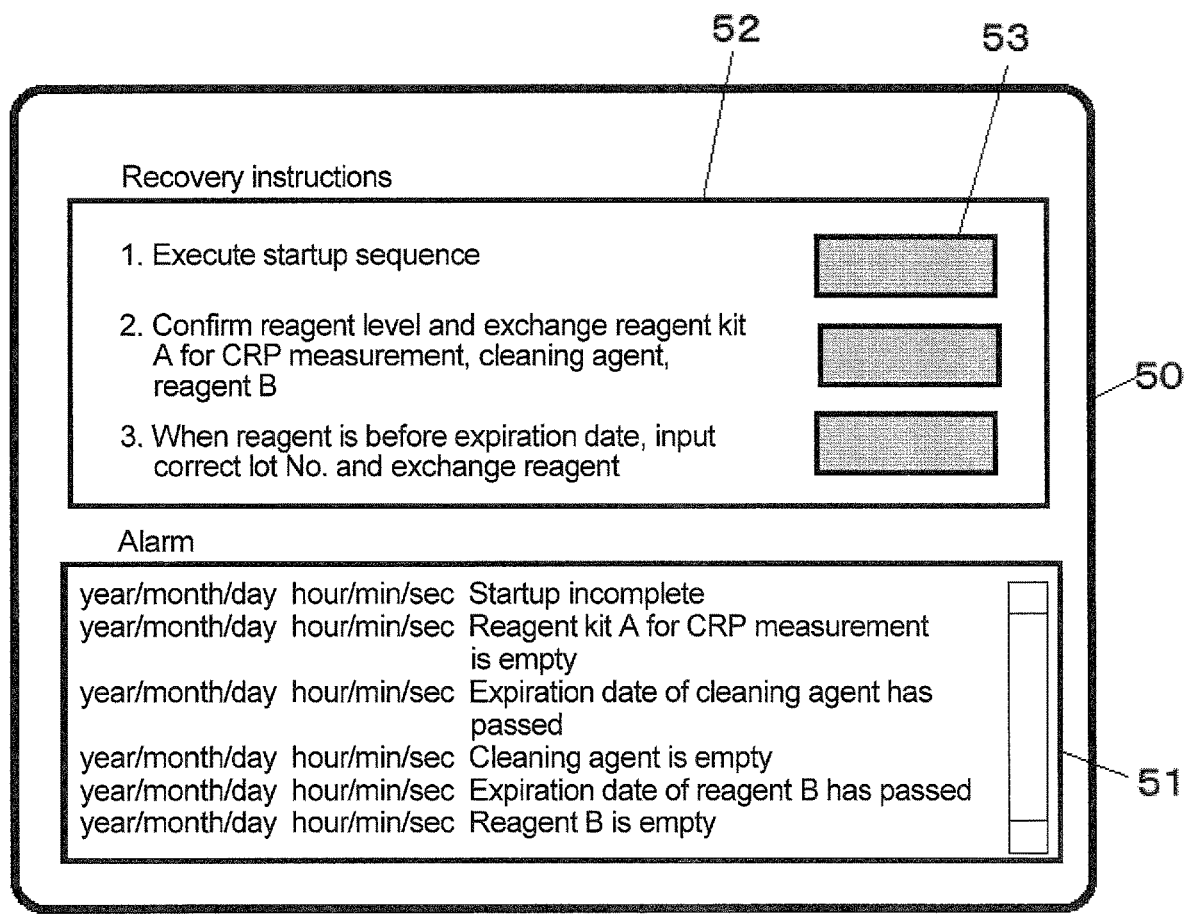
FIG. 3 shows one embodiment of the guidance window in the specimen analysis apparatus according to the present invention.

The display part 200 displays, for example, as shown in FIG. 3, a guidance window 50 including an alarm display region 51 and a recovery operation display region 52 displays the name of the failure as an alarm in the alarm display region 51, and displays a sentence of recovery operation on the recovery operation display region 52. In the example of FIG. 3, the recovery operation display region 52 displays above the alarm display region 51 in the guidance window 50; however, such layout is not limitative. A layout permitting visual recognition at first sight that alarm display region 51 and recovery operation display region 52 are mutually related is preferable.

The alarm display region 51 displays alarms of all failures occurring at the moment. When only one failure has occurred, one alarm of the failure that has occurred is displayed in the alarm display region 51. In FIG. 3, alarms indicating the names of the failures that have occurred in the measuring part 100, "Startup incomplete", "Reagent kit A for CRP is empty", "Expiration date of cleaning agent has passed", "Cleaning agent is empty" and "Expiration date of reagent agent B has passed" are displayed along with the times of occurrence of the failures. The user looking at the alarm display region 51 can confirm that the failures of "Startup incomplete", "Reagent kit A for CRP is empty", "Expiration date of cleaning agent has passed", "Cleaning agent is empty" and "Expiration date of reagent agent B has passed" have occurred in chronological order.

In step S5, the following analysis processing is performed to determine the contents of display of the recovery operation displayed in the recovery operation display region 52.

Processing 1

Whether one alarm or multiple alarms have occurred is determined. When one alarm has occurred, a recovery operation including a given operation stored in the storage part for cancelling the alarm is displayed as it is in the recovery operation display region 52. When multiple alarms have occurred, all recovery operations (multiple recovery operations) of the multiple alarms are comprehensively analyzed and, when the multiple recovery operations include a recovery operation having the same operation, and revision to subtract the same operation from at least one recovery operation in the recovery operations having the same operation is performed. That is, for example, when two recovery operations contain the same operation, the same operation is subtracted from either one of the two recovery operations. When three recovery operations contain the same operation, the same operation may be subtracted from two out of the three recovery operations.

For example, a recovery operation for cancelling an alarm for a failure of "detection of original point of motor failed" and a recovery operation for cancelling an alarm for a failure of "breakdown of specimen holder" each contain "execution of sequence of auto control for returning motor to given position (sequence 1)". Therefore, when these two alarms have occurred, an operation to execute the sequence in either one of the recovery operations is subtracted.

A recovery operation for cancelling an alarm for a failure of "temperature control is incomplete" is "execution of sequence of startup for filling piping with liquid and preparing for measurement (sequence 2). The "startup" contains the above-mentioned action of "auto control". Therefore, for example, when the alarm of "temperature control is incomplete" and the above-mentioned alarm(s) of "detection of original point of motor failed" and/or "specimen holder breakdown" have occurred, sequence 1, which is the lower sequence, is subtracted from these recovery operations.

Processing 2

All recovery operations (multiple recovery operations) of all the multiple alarms are comprehensively analyzed and the priority order of the recovery operations to be executed is determined. For example, as mentioned above, when alarm 1 for the failure of "reagent shortage" and alarm 2 for the failure of "door of apparatus is open" have occurred, recovery operations are executed in the order of recovery operation 2 for cancelling alarm 2 ("close door of apparatus") and recovery operation 1 for cancelling alarm 1 ("replace reagent and execute blank measurement").

In step S6, the recovery operations with the priority order determined by the analysis processing in step S5 are displayed, together with the command buttons for execution of respective recovery operations, on the display part 200 in a manner clarifying the priority order (order to be executed).

In the example of FIG. 3, numbers indicating the order of priority of execution are added to the beginning of respective recovery operations in the recovery operation display area 52, and the recovery operations are displayed in the order of one with higher priority to one with lower priority in the recovery operation display area 52, so that the order of priority (priority order) of the recovery operations to be executed may be clear to the user. In addition, a command button 53 for instructing the execution of the recovery operation is displayed adjacent to the display of each recovery operation, thereby enabling rapid execution of the recovery operation. When a command button for instructing the execution of the recovery operation is located apart from the display part of the apparatus, even when the order of priority (priority order) of the recovery operations to be executed may be known by looking at the display part, the recovery operations cannot be executed immediately in the priority order. The present invention can also solve such problem. The multiple recovery operations may not be displayed side by side at once as in FIG. 3. They may be displayed one by one from one with higher priority. In this case, one recovery operation is executed, after which the next recovery operation is displayed. In addition, multiple recovery operations may be displayed instead of one at a time. In this case, multiple recovery operations to be displayed are in the descending order of priority. Furthermore, after executing all of the displayed multiple recovery operations, multiple recovery operations with the next highest priority may be displayed. Alternatively, after executing one of the displayed multiple recovery operations, one recovery operation with the next highest priority may be displayed. In this manner, multiple recovery operations are displayed in the order of higher priority to lower priority.

By the foregoing processing, when failures occur in the measuring part 100, the occurrence of failures (alarms) and recovery operations for solving the failures (recovery operations to cancel alarms) are displayed in the guidance window 50 of the display part 200, and the user can recognize the priority order of the recovery operations and execute the recovery operations rapidly according to the priority order.

In addition, the command buttons 53 displayed next to the display of each recovery operation displayed in the above-mentioned recovery operation display region 52 can be made to be inactive except a command button pressed for a recovery operation under execution. Using buttons of such embodiment, execution of recovery operations in an incorrect order different from the priority order of the recovery operations can be prevented. The command buttons 53 may disappear from the button display after completion of execution of the recovery operation. Using buttons of such embodiment, incorrect execution of a recovery operation after completion of the execution thereof can also be prevented.

Figure 4:
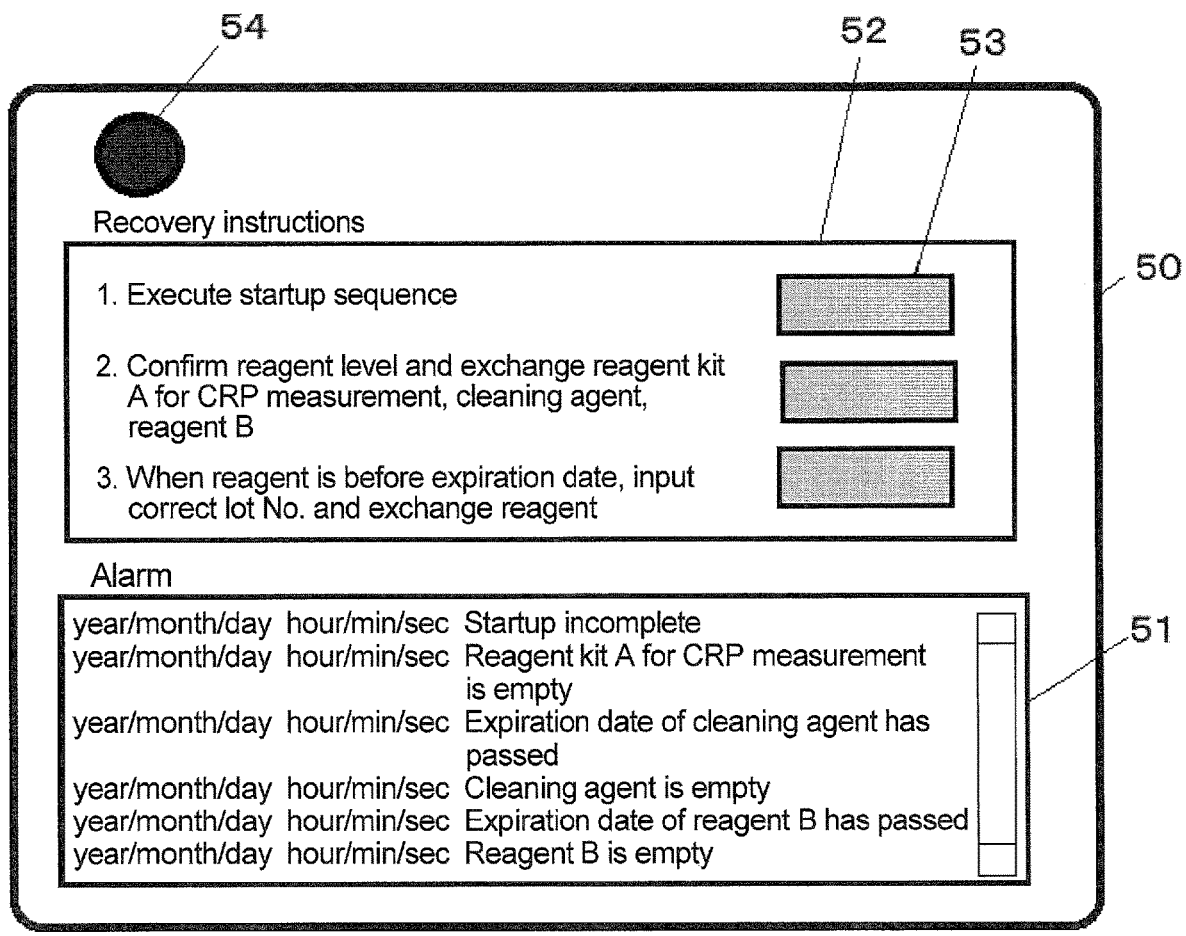
FIG. 4 shows other embodiment of the guidance window in the specimen analysis apparatus according to the present invention.

FIG. 4 shows other example of the guidance window display to be displayed in the part of the specimen analysis apparatus according to the present invention. FIG. 4 is different from FIG. 3 in that it displays a marker 54 distinguishing whether or not the measuring part 100 can perform measurement in a region different from the alarm display region 51 and recovery operation display region 52 in the guidance window. That is, when an alarm is displayed in the alarm display region 51 and the measuring part 100 can perform measurement, the marker 54 lights up in yellow, when the measuring part 100 cannot perform measurement, the marker 54 lights up in red, and when an alarm is absent in the alarm display region 51, the marker 54 itself disappears.

The failures occurring in the measuring part 100 include, for example, those preventing specimen measurement unless the failure thereof such as hemolysis reagent liquid runout and the like has been resolved (i.e., without execution of recovery operation to cancel alarm) and, for example, those permitting specimen measurement even when the failure thereof such as expiration date of reagent passed and the like has not been resolved (i.e., without execution of recovery operation to cancel alarm). When the specimen analysis apparatus according to the present invention has the embodiment of FIG. 4 having a guidance window displayed and when, for example, an alarm has occurred but there is a request to collect specimen measurement data without giving much weight to the importance of data reliability, the user looking at the display part can know whether the specimen can be measured without executing a recovery operation of the alarm, thus enabling flexible response meeting the situation. In the guidance window of FIG. 4, when an alarm is displayed in the alarm display region 51 and the measuring part 100 can perform measurement, the marker 54 lights up in yellow, when the measuring part 100 cannot perform measurement, the marker 54 lights up in red, and when an alarm is absent in the alarm display region 51, the marker 54 itself disappears. Failure (alarm) and recovery operation The failure displayed as alarm on the display part 200 and recovery operation to be executed for cancelling the alarm in the specimen analysis apparatus according to the present invention include the following besides those mentioned above.

(1) Failure: "door of cool box for CRP is open", recovery operation: "close door of cool box"

(2) Failure: "position of specimen holder is incorrect", recovery operation: "open specimen holder and adjust position"

(3) Failure: "waste liquid tank is full", recovery operation: "discard waste liquid in tank"

(4) Failure: "temperature control incomplete", recovery operation: "confirm room temperature"

(5) Failure: "battery runout", recovery operation: "replace battery and set time"

Detailed Constitution of Measuring Part

In the embodiment of FIG. 1, the measuring chamber 20 is constituted to perform analysis methods such as impedance method (electric resistance method), flow cytometry (optically particle analyzing method), light-focused flow impedance method (method for performing impedance method and flow cytometry in single flow path) and the like according to the object of analysis (blood cells count, classification of white blood cell, immunoassay and the like). Nozzle 11 moves in the horizontal direction or vertical direction due to the operation of driving unit 12, lower end side of the nozzle enters into a specimen container 25 or each measuring chamber 20, and sucks or discharges liquid. The measuring chamber 20 controlled by a control part 30 performs a measurement action for analysis and sends the measurement data to the control part 30. The control part 30 processes the received measurement data, performs analysis such as frequency distribution and the like, and outputs the analysis results. As for the structure of each part of the measuring part 100 and action for the measurement (action of nozzle, action for measurement in each measuring chamber, action of various pumps and electromagnetic valve device), and calculation process for analysis in the control part 200, conventionally-known techniques for automatic analysis apparatuses in patent document 1 and the like can be referred to.

In the blood analysis apparatus shown in FIG. 1, a nozzle 11 sucks only a given amount of a specimen (blood) contained in a specimen container, and distributes same to a measuring chamber 20. In the example of FIG. 1, BASO chamber 21, LMNE chamber 22, RBC chamber 23, WBC chamber 24 are provided as the measuring chamber 20. In this constitution, a flow cell (not shown) is connected to the LMNE chamber, a necessary processing with a reagent is performed, a light-focused flow impedance method is performed in the flow cell, and lymphocytes, monocytes, neutrophils and eosinophils are counted. As shown in patent document 1, a measuring chamber for immunoassay such as measurement of CRP value and the like or a cleaning chamber for washing blood adhering to the nozzle and for discharging excess blood specimen in the nozzle may be provided in addition to these measuring chambers. The measuring chamber may also serve as the cleaning chamber.

In each measuring chamber in which the specimen is distributed, the count data peculiar to each measuring chamber is acquired under the control of the control part. In the control part, each count data sent from each measuring chamber is processed. In, for example, blood analysis, white blood cell count, red blood cell count, hemoglobin concentration, hematocrit value, average red blood cell volume, mean corpuscular hemoglobin, mean corpuscular hemoglobin concentration, platelet count, red blood cell distribution width, mean platelet volume, platelet distribution width, platelet crit, lymphocyte count, lymphocyte ratio, monocyte count, monocyte ratio, granulocyte count, granulocyte ratio, neutrophil count, neutrophil ratio, eosinophil count, eosinophil ratio, basophil count, basophil ratio, CRP value (C-reactive protein concentration), blood glucose level, and the like are analyzed.

The specimen may be an inorganic specimen such as glass particles, ceramic particles and the like, in addition to specimen of biological origin such as blood, urine, feces, cell and the like. A measuring chamber can be provided according to a specimen to be analyzed, and a control part can be constituted according to the analysis of a specimen.

INDUSTRIAL APPLICABILITY

According to the present invention, there is provided an automatic analysis apparatus enabling the user to recognize, when multiple alarms have occurred and multiple recovery operations should be performed, the priority order of multiple recovery operations and rapidly execute the recovery operations in that priority order.

This application is based on a patent application No. 2017-138411 filed in Japan (filing date: Jul. 14, 2017), the contents of which are incorporated in full herein.

The invention claimed is:
1. A specimen analysis apparatus, comprising:
a measuring part for performing measurement for specimen analysis;
a display part; and
a control part, wherein
the control part:
    controls the measuring part and analyzes measurement data from the measuring part,
    displays on the display part an alarm display region displaying an alarm of a failure occurred in the measuring part, and a recovery operation display region displaying a recovery operation to cancel the alarm displayed in the alarm display region,
    when multiple alarms have occurred, displays multiple recovery operations to cancel them in the order of from higher priority to lower priority,
    prior to execution of one or more of the multiple recovery operations, performs a revision to subtract a duplicate operation from the multiple recovery operations, and
    after the revision, displays, together with the multiple recovery operations, multiple command buttons such that every recovery operation of the multiple recovery operations is arranged in a pair with a respective command button of the multiple command buttons at a position adjacent to the display of the respective recovery operation, each command button being for instructing execution of the respective recovery operation.

2. The specimen analysis apparatus according to claim 1, wherein the command buttons for the multiple recovery operations turn inactive except a command button pressed for a recovery operation under execution.

3. The specimen analysis apparatus according to claim 1, wherein the control part displays a marker indicating whether or not the measuring part is capable of measurement while the alarm is displayed in the alarm display region.

* * * * *